Figure 1:
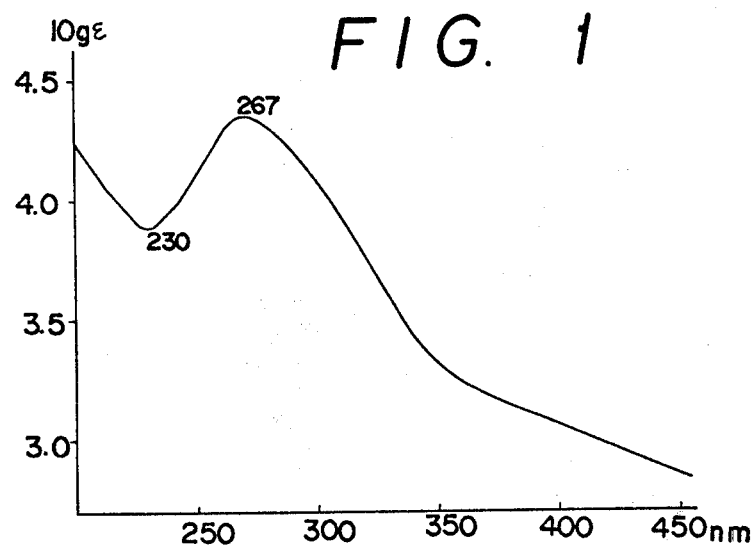

United States Patent [19]

Arai

[11] 4,248,863

[45] Feb. 3, 1981

[54] ANTIBIOTICS SAFRAMYCINS A, B, C, D AND E AND PROCESS FOR PRODUCING THE SAME

[76] Inventor: Tadashi Arai, No. 50-6, 6-chome, Nogata, Nakano-ku, Tokyo, Japan

[21] Appl. No.: 940,031

[22] Filed: Sep. 6, 1978

[30] Foreign Application Priority Data

Sep. 12, 1977 [JP] Japan ................................ 52/109692

[51] Int. Cl.³ .............................................. A61K 35/00
[52] U.S. Cl. .................................... 424/121; 424/122; 435/169
[58] Field of Search ............. 424/121, 120; 195/80 R; 435/169

[56] References Cited

U.S. PATENT DOCUMENTS

| | | | |
|---|---|---|---|
| 4,081,531 | 3/1978 | Arai | 424/121 |
| 4,127,446 | 11/1978 | Arai | 424/121 |

OTHER PUBLICATIONS

Miller, The Pfizer Handbook of Microbial Metabolites, McGraw-Hill Book Co., Inc., New York, N.Y., 1961 pp. 352-354.

*Primary Examiner*—Jerome D. Goldberg
*Attorney, Agent, or Firm*—Frishauf, Holtz, Goodman & Woodward

[57] ABSTRACT

Antibiotic substances named saframycins A, B, C, D and E having antibacterial activity and activity against transplantable tumors. It is produced by cultivation of *Streptomyces lavendulae* strain No. 314.

10 Claims, 15 Drawing Figures

ANTIBIOTICS SAFRAMYCINS A, B, C, D AND E AND PROCESS FOR PRODUCING THE SAME

This invention relates to new antibiotic substances saframycins A, B, C, D and E and a process for producing the same.

More particularly, it is concerned with a new group of antibiotic substances named saframycins A, B, C, D and E, respectively, having antibacterial activities mainly against gram-positive bacteria and activity against transplantable trimers. It is also concerned with a process for the production of antibiotic substances, saframycins A, B, C, D and E, which comprises cultivating *Streptomyces lavendulae* strain No. 314, recovering a complex of saframycins A, B, C, D and E from a cultured broth and then isolating saframycins A, B, C, D and E from said complex.

Heretofore, isolation of about 3,000 different types of antibiotic substances has been reported and it has become difficult in the art to find out a new antibiotic substance. However, a new antibiotic substance has been increasingly needed due to appearance of those microorganisms resistant to conventional antibiotics as well as manifestation of new infectious diseases caused by the widespread application of antibiotics having a broad antibacterial spectrum, steroidal hormones, antitumor agents or antiimmune substances.

The present inventor found formerly that *Streptomyces lavendulae* can produce some antibiotic substances, mimosamycin and chlorocarcins A, B and C (Japanese Patent Application No. 113289/1975 filed on Sept. 19, 1975 and laid open to public on Mar. 24, 1977 as No. 38094/1977). Said mimosamycin and chlorocarcins A, B and C are disclosed in U.S. Pat. Nos. 4,081,531 and 4,127,446.

Thereafter, the present inventor has made further studies on the products obtained by cultivating the actinomycetes and, as a result, it has now been found that the actinomycetes capable of producing known antibiotic substances can also produce new and useful antibiotic substances, saframycins A, B, C, D and E and also that *Streptomyces lavendulae* strain No. 314 can particularly produce these antibiotic substances at a high level of activity.

It is, accordingly, a primary object of this invention to provide new antibiotic substances saframycins A, B, C, D and E which show valuable biological activities.

Another object of this invention is to provide a process for the fermentative production of these new antibiotics.

These and other objects and advantages of this invention will be apparent from the description as stated below.

*Streptomyces lavendulae* strain No. 314 in this invention was isolated from a soil sample collected at Kyoto and belongs to the genus Streptomyces. This strain has been deposited under the accession No. 3218 in Technical Research Institute of Microbial Industry, Agency of Industrial Science & Technology, Ministry of International Trade and Industry, Japan and also as NRRL-11002 in the Northern Regional Research Laboratory, Northern Central Region, Agricultural Research Service, United States Department of Agriculture, at Peoria, Ill., U.S.A.

Observation of aerial mycelium and spore of *Streptomyces lavendulae* strain No. 314 was effected by cultivating the strain on the media according to the methods of the International Streptomyces Project (ISP) (Shirling. E. B. & D. Gottlieb; International J. Systematic Bacteriol. 16, 313–340, 1966); namely, by cultivating on agar plates of yeast-starch-agar medium, inorganic salts-starch-agar medium and maltose-containing basal medium for carbon source utilization pattern (Pridham-Gottlieb's agar medium) at 27° C. for 1–2 weeks. Also, colors of mycelium with mature spores, vegetative mycelium and others were determined according to the color chip number as taught in "Descriptive Color Name Dictionary", Container's Corporation of America, 1950 and "Color Harmony Manual", Container's Corporation of America, 1958.

The strain No. 314 develops wave-shaped folded aerial mycelium long-branched in a diameter of about $0.6–1.0\mu$ with many cylindrical spores. Spores are $0.6–1.0\mu \times 0.8–2.0\mu$ in size. According to the standard in ISP, the strain having the above morphological characteristics is said to belong to the Section Rectiflexibiles. However, the aerial hyphae are with loops or incomplete or elongated spirals which are in coils of 1–2 turns. Therefore, the strain No. 314 has been morphologically determined to belong to the Section Retinaculiaperti. When spore surface on these media are observed under electron microscope, the spore of the strain has been found to have a smooth surface. The strain No. 314 has main characteristics in that the aerial hyphae are morphologically of the Section Retinaculiaperti, color of the aerial hyphae with mature spores is rose to lavender on various media, color of the vegetative mycelium is sometimes blue to bluish brown on a synthetic medium and production of melanin pigment is positive. Then, searching the strains of the genus Streptomyces which are described in "The Actinomycetes", S. A. Waksman, Vol. 2, 1959 and "Bergey's Determinative Bacteriology", 8th Ed., 1974, it has been suspected that the strain has close resemblance to *Streptomyces lavendulae*. The strain No. 314 is inoculated to a conventional medium for producing an antibiotic substance and shaken culture is effected at 27° C. for a cultivation period of 18 to 72 hours to produce a culture filtrate having a high activity against coliform bacilli. The filtrate thus obtained is treated with active charcoal under alkaline condition, eluted with acidic acetone or adsorbed on a weak cation exchange resin, for example, Amberite IRC-50 (trade name, available from Rohm & Haas Co. U.S.A.) and subjected to desorption with 0.1 N hydrochloric acid to afford an antibacterial substance against coliform bacilli. Then, the substance thus obtained is purified by chromatography over, for example, Amberite CG-50 (trade name, available from Rohm & Haas Co.) and crystallized in the form of its Reinecke's salt or picrate, whereupon this substance is identified as streptothricin.

Further, comparison of cultural and physiological characteristics was made by the use of *Streptomyces lavendulae* IFM 1031, which is a streptothricin-producing strain, *Streptomyces racemochromogenes* IFM 1081, which is considered to be identical with *Streptomyces lavendulae* and capable of producing streptothricin, and the present strain for final identification. The results are summarized in Tables 1, 2 and 3. More specifically, the strain No. 314 has been identical with *Streptomyces lavendulae* in every characteristic property which is presently applied for identification of the strain in the genus Streptomyces, though minor differences are observed in some respects, for example, utilization of L-arabinose and the like, and thus the strain has been identified as *Streptomyces lavendulae*. Also, *Streptomyces racemochromogenes* can produce streptothricin, but this strain is apparently different from the strain No. 314 which is *Streptomyces lavendulae* from the above-mentioned comparison results.

TABLE 1

Comparison of Streptomyces strain No. 314 with known strains - 1

| Medium | | Strain No. 314 | | Streptomyces lavendulae IFM 1031 | | Streptomyces racemo-chromogenes IFM 1081 |
|---|---|---|---|---|---|---|
| Sucrose-nitrate agar (Czapek's medium) | AM | abundant, white to ivory (2 db) | AM | abundant, ivory (2 db) to gray (3 dc) | AM | abundant, ivory (2 db) to gray (5 dc) |
| | VM | spreading growth, colorless to faint olive (1½ ie) | VM | spreading growth, colorless to faint brown | VM | faint brown to purple brown (11 nl) |
| | DP | none, or faint brown | DP | faint brown | DP | faint brown |
| Glucose-asparagine agar (Krainsky) | AM | abundant, pink to lavender (5 ge) | AM | abundant, pink to lavender (5 ge) | AM | abundant, pink to lavender (5 ge) |
| | VM | spreading growth, colorless to faint olive (1½ ie) | VM | spreading growth, bluish blue (10 pn) | VM | spreading growth, brown to blue (10 pn) |
| | DP | none, or faint brown | DP | none, or faint brown | DP | none, or faint brown |
| Glycerol-asparagine agar (ISP) | AM | moderate, faint brownish gray to silver gray (3 fe) | AM | small amount, silver gray (3 fe) | AM | moderate, silver gray (3 fe) |
| | VM | spreading growth, colorless, sometimes blue colonies | VM | olive to bluish blue (1½ pn) | VM | dark olive (1½ pn) |
| | DP | none | DP | faint brown | DP | faint olive brown |
| Calcium-maleate agar | AM | moderate, powdery, pink (3 ba) | AM | none | AM | none |
| | VM | spreading growth, dark olive (1½ nl) | VM | spreading growth, bluish brown (3 pn) | VM | spreading growth, bluish brown (3 pn) |
| | DP | none, or faint bluish brown | DP | faint brown | DP | faint olive brown |
| Inorganic salts-starch agar (ISP) | AM | abundant, yellowish gray (3 dc) | AM | abundant, gray (3 dc) | AM | abundant, gray (3 dc), bluish gray (2 po) |
| | VM | colorless | VM | colorless to dark olive (2 po) | VM | dark olive (2 po) |
| | DP | none | DP | none | DP | faint olive brown |

Comparison of streptomyces strain No. 314 with known strains - 2

| Nutrient agar | AM | none | AM | none | AM | none |
|---|---|---|---|---|---|---|
| | VM | spreading growth, glistening surface, camel (3 ie) | VM | spreading growth, glistening surface, camel (3 ie) | VM | spreading growth, glistening surface, camel (3 ie) |
| | DP | faint brown | DP | faint brown | DP | faint brown |
| Yeast extract-malt extract agar (ISP) | AM | abundant, spots with pink to white (5 ge) | AM | abundant, pink (5 ge) | AM | abundant, pink (5 ge) |
| | VM | folded, colorless to faint brown | VM | spreading growth, colorless to faint brown | VM | folded, faint brown |
| | DP | dark brown (4 pi) | DP | dark brown (4 pi) | DP | dark brown (4 pi) |
| Oatmeal agar (ISP) | AM | moderate, white to pink (4 ca) | AM | moderate, pink to lavender (5 ec) | AM | moderate, pink (3 ca) |
| | VM | colorless | VM | blue (15 ni) | VM | bluish brown (15 ni) |
| | DP | none | DP | none, or bluish brown | DP | none, or faint brown |
| Egg medium | AM | none | AM | poor, white | AM | poor, to none |
| | VM | much folded, chocolate (4 pl) | VM | much folded, chocolate (4 pl) | VM | much folded, chocolate (4 pl) |
| | DP | chocolate brown | DP | chocolate brown | DP | chocolate |
| Tyrosine synthetic medium | AM | abundant, pink (7 ge) | AM | abundant, pink (7 ge) | AM | abundant, pink (7 ge) |
| | VM | spreading growth, mustard brown (2 ni) | VM | spreading growth, mustard brown (2 ni) | VM | spreading growth, mustard brown (2 ni) |
| | DP | none, or faint brown | DP | none, or faint brown | DP | none, or faint brown |

AM: aerial mycelium
VM: vegetative mycelium
DP: water-soluble pigment (color of medium)

TABLE 2

Comparison of physiological properties of Streptomyces strain No. 314 with known strains

| Physiological property | Strain No. 314 | Streptomyces lavendulae IFM 1031 | Streptomyces racemochromogenes IFM 1081 |
|---|---|---|---|
| Nitrate reduction (14 days) | + | + | + |
| Liquefaction of gelatin (18° C., 21 days) | + | + | + |
| Soluble pigment | brown | brown | brown |
| Hydrolysis of cellulose (21 days) | − | − | − |
| Litmus milk | | | |
| Coagulation | ++ | ++ | ++ |
| Peptonization | ++ | ++ | ++ |
| pH | 8.0 | 7.8 | 7.8 |
| Melanin formation | + | + | + |

TABLE 3

Comparison of carbon source utilization pattern of Streptomyces lavendulae strain No. 314 with known strains

| Carbon source | Strain No. 314 | Streptomyces lavendulae IFM 1031 | Streptomyces racemochromogenes IFM 1081 |
|---|---|---|---|
| D-xylose* | − | + | |
| L-arabinose* | + | − | |
| L-rhamnose* | − | − | |
| D-glucose* | + | + | + |
| D-fructose* | + | + | |
| sucrose* | + | + | + |
| lactose | − | − | − |
| maltose | + | + | + |
| raffinose* | | | − |
| mannitol* | | | |
| i-inositol* | | − | |
| sodium acetate | + | + | + |
| sodium citrate | + | + | + |
| sodium succinate | + | + | + |
| Control | − | | |

*carbon source described in ISP.

The saframycin complex which can be produced according to this invention has not yet been isolated from a cultured broth of the aforesaid well-known microorganisms belonging to *Streptomyces lavendulae.*

According to the process of this invention, saframycin complex can be produced by cultivation of *Streptomyces lavendulae* strain No. 314.

Cultivation may be principally conducted according to conventional cultivation procedures of a microorganism, but it is usually favourable to effect submerged culture in a liquid medium. As the medium which may be employed in this invention, there may be any media containing nutrients which the strain No. 314 of the genus Streptomyces may utilize. More specifically, synthetic, semi-synthetic or natural media may be used and, as examples of medium components, there may be mentioned a carbon source, such as glucose, maltose, fructose, xylose, starch, glycerol and the like; a nitrogen source, such as meat extract, peptone, gluten meal, cotton seed oil, soybean meal, corn steep liquor, dry yeast extract, ammonium sulfate, ammonium chloride, urea and other organic or inorganic nitrogen sources. Carbonates, phosphates or other salts of metals may be additionally incorporated into a medium. Where an excessive foaming is observed during cultivation, it is convenient to add to a medium an antifoaming agent, such as a vegetable oil, e.g., soybean oil; silicone oil; polyoxyalkylene type agents; mineral oils and the like.

Cultivation temperature is usually within a range of about 27°–30° C. As a volume of the medium is increased, it is suitable to effect seed cultures and then inoculate the seed cultures to a fomentation medium. Cultivation time is usually from about 18 hours to about 24 hours.

The aforesaid culture conditions may be selected for optimum and applied depending upon the microorganism to be used for production of the present antibiotics.

The antibiotic substances thus accumulated in a cultured broth are usually included within mycelia and culture liquid and extracted from the mycelia collected by centrifugation or filtration and the filtrate thus recovered. More specifically, the present antibiotic substances may be isolated, recovered and purified by conventional procedures commonly employed for the production of a natural product, for instance, those of utilizing solubility and solubility difference in suitable solvents, separability and difference in a separating rate from a solution, difference in adsorption and affinity on various adsorbents, difference in distribution between two liquid phases and the like. These procedures may be applied, if desired, alone or in optional combination therewith or repeatedly. A representative procedure will be set forth below.

After completion of the cultivation, the cultured broth is filtered to separate mycelia from the filtrate. The filtrate is adjusted to pH 8.0 with 10 N sodium hydroxide. The filtrate may be previously concentrated to ½–⅓ volume for better extraction efficiency with a solvent. In the solvent extraction as noted above, basic, water-soluble antibiotics, for example, streptothricin simultaneously produced by the strain No. 314 are left in the filtrate, while saframycin complex and the like are extracted into the solvent phase. The solvent phase is concentrated to dryness under reduced pressure, the concentrate is dissolved in a small amount of ethyl acetate, the solution is shaken with aqueous sodium carbonate and separated, whereupon acidic substances are transferred into an aqueous phase. The solvent phase is extracted with 1 N hydrochloric acid, adjusted to pH 9–10 with aqueous ammonia and extracted with chloroform. This step is repeated several times and the solvent phase is concentrated to dryness under reduced pressure to give a crude basic component containing saframycin complex. The component is column-chromatographed over silica gel with a mixture of benzene and ethyl acetate to give a fraction predominantly containing saframycin A. These fractions, are treated by a Sephadex LH-20 (available from Pharmacia Co., Ltd., Sweden) column chromatography with methanol as an eluent to afford saframycin A as a yellow syrup, which is then treated with a cold ether to form a yellow powder.

The chromatography column initially eluted is further eluted with a mixture of ethyl acetate and methanol to give a fraction predominantly containing saframycins B, C, D and E. These fractions are concentrated to dryness to give a mixture of saframycins B, C, D and E, which is then purified by a column-chromatography of silica gel and a subsequent column-chromatography on Sephadex LH-20 and methanol as an eluent to give saframycins B, C, D and E as yellow powders. Saframycins B, C and D are obtained from ether elution as orange-yellow prisms, orange-red needles and yellow needles, respectively. Saframycin E is obtained from acetone elution as a yellow powder.

Saframycins A, B, C, D and E are basic antibiotic substances and thus capable of forming the corresponding acid addition salts, which are intended to fall under the scope of this invention. Typical examples of such acid addition salts are those formed with hydrochloric acid, sulfuric acid, phosphoric acid, stearic acid, propionic acid, tartaric acid, maleic acid and the like. As can be expected, the salts of this sort can exert the same antibiotic activity as the free antibiotic substances do, but there may be usually seen differences in activity and solubility property between them. Physico-chemical properties of saframycins A, B, C, D and E are summarized as hereunder.

Figure 2:
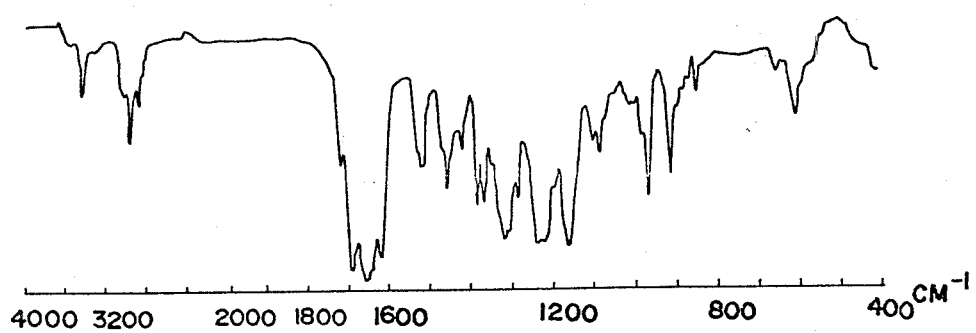
Figure 3:
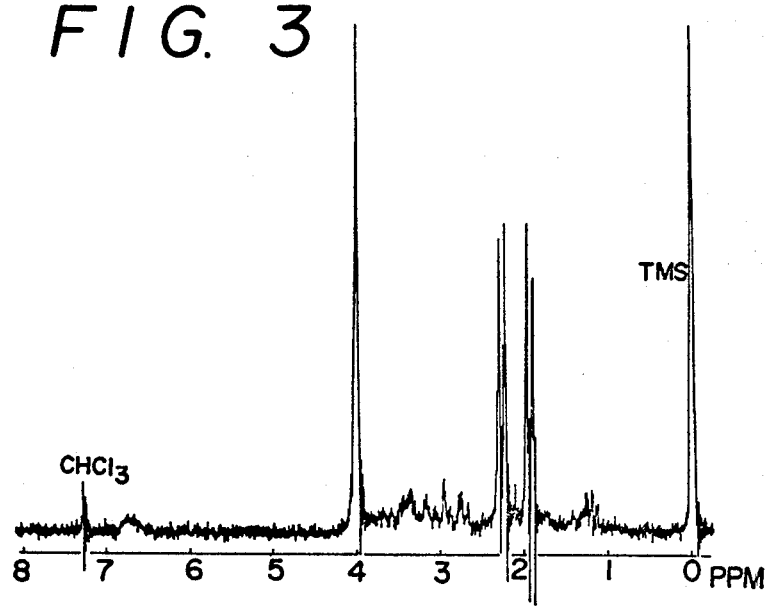

[A] Physico-chemical properties of saframycin A
 ① Color and appearance
  Yellow powder in saframycin A base form
 ② Melting point
  122°-126° C.
 ③ Elementary analysis
  C: 61.47%, H: 5.41%, N: 9.33%
 ④ Molecular weight (Mass-spectrum)
  562
 ⑤ Empirical formula
  $C_{29}H_{30}N_4O_8 \cdot 2/5\ H_2O$
 ⑥ Specific rotation
  $[\alpha]_D^{20} = +18.2°$ (C=1.0, methanol)
 ⑦ Ultraviolet absorption spectrum (as shown in FIG. 1)
  UV $\lambda_{max}^{methanol}$ nm (log ε): 267 (4.34)
  $\lambda_{min}^{methanol}$ nm (log ε): 230 (3.88)
 ⑧ Infrared absorption spectrum (as shown in FIG. 2)
  IR $\nu_{max}^{CHCl_3}$ cm$^{-1}$: 3400, 1716, 1685, 1660, 1615
 ⑨ NMR spectrum (CDCl$_3$) (as shown in FIG. 3)
  δ: 1.90 (3H, S), 1.98 (3H, S), 2.24 (3H, S), 2.30 (3H, S), 4.04 (6H, S), 6.65 (3H, bs).
 ⑩ Solubility
  Easily soluble: Esters, chloroform, acetone, alcohols
  Sparingly soluble: Ethyl ether
  Insoluble: Water, n-hexane
 ⑪ Color reaction
  Positive in Dragendorff reaction; negative in ninhydrin, perchloroiron and anthrone reactions

Figure 4:
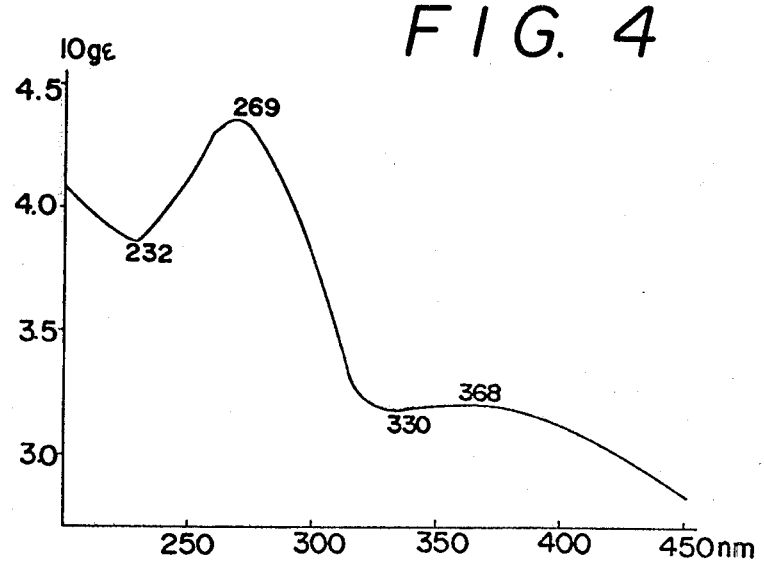
Figure 5:
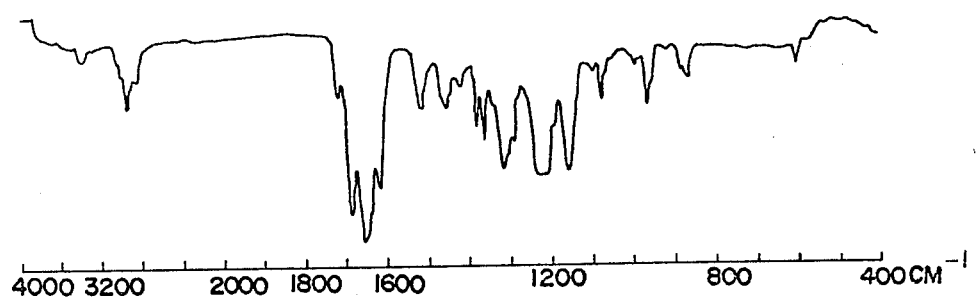
Figure 6:
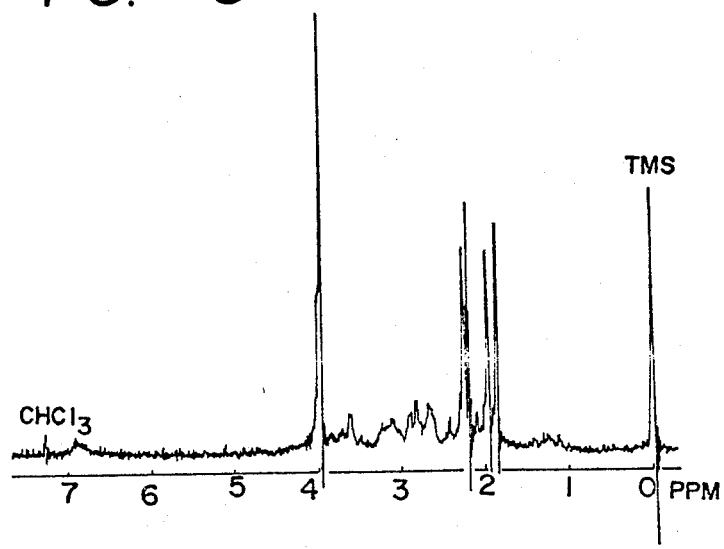

[B] Physico-chemical properties of saframycin B base
 ① Color and appearance
  orange-yellow prisms
 ② Melting point
  108°-109° C.
 ③ Elementary analysis
  C: 62.36%, H: 5.71%, N: 7.66%
 ④ Molecular weight (Mass spectrum)
  537
 ⑤ Empirical formula
  $C_{28}H_{31}N_3O_8$
 ⑥ Specific rotation
  $[\alpha]_D^{20} = -54.4$ (C=1.0, methanol)
 ⑦ Ultraviolet absorption spectrum (as shown in FIG. 4)
  UV $\lambda_{max}^{methanol}$ nm (log ε): 269 (4.35), 368 (3.13).
  $\lambda_{min}^{methanol}$ nm (log ε): 232 (3.86), 330 (3.10).
 ⑧ Infrared absorption spectrum (as shown in FIG. 5)
  IR $\nu_{max}^{CHCl_3}$ cm$^{-1}$: 3430, 1720, 1690, 1660, 1620.
 ⑨ NMR spectrum (CDCl$_3$) (as shown in FIG. 6)
  δ: 1.90 (3H, S), 1.98 (3H, S), 2.23 (3H, S), 2.28 (3H, S), 4.00 (6H, S), 6.28 (1H, bs).
 ⑩ Solubility
  Easily soluble: Lower alcohols, chloroform, esters, acetone, benzene
  Sparingly soluble: Ethyl ether
  Insoluble: Water, n-hexane
 ⑪ Color reaction
  Positive in Dragendorff and Meyer reactions, negative in ninhydrin and Ehrlich reactions

Figure 7:
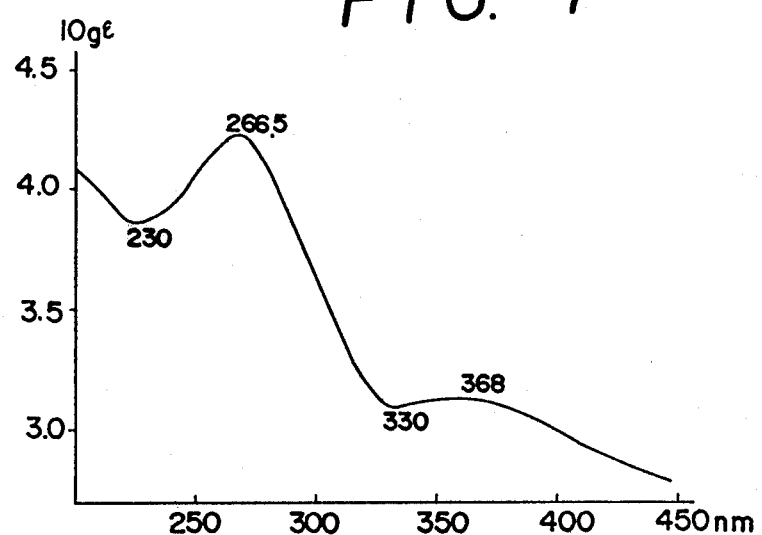
Figure 8:
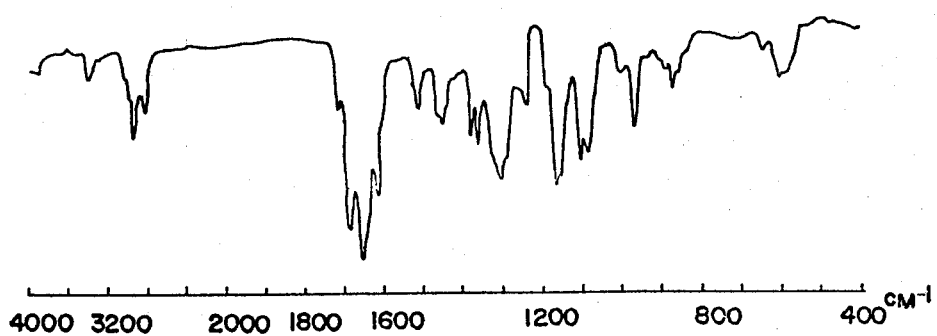
Figure 9:
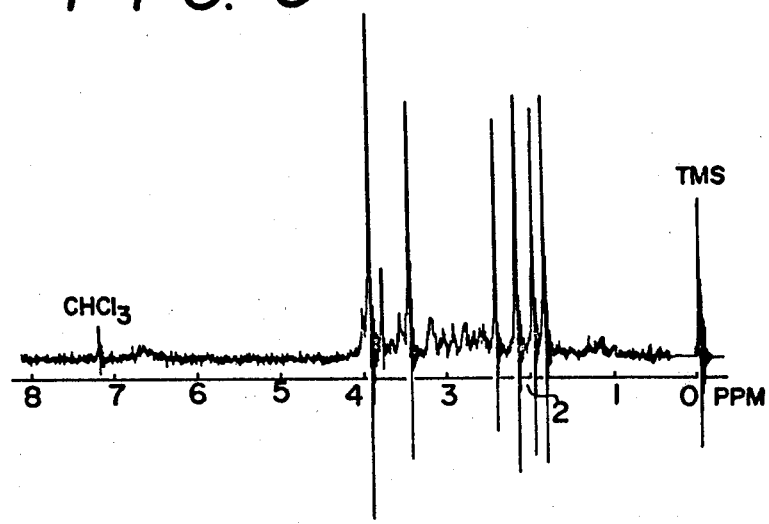

[C] Physico-chemical properties of saframycin C base
 ① Color and appearance
  Orange-red needles
 ② Melting point
  143°-146° C.
 ③ Elementary analysis
  C: 61.61%, H: 5.96%, N: 7.39%
 ④ Molecular weight (Mass spectrum)
  567
 ⑤ Empirical formula
  $C_{29}H_{33}N_3O_9$
 ⑥ Specific rotation
  $[\alpha]_D^{20} = -20.8°$ (C=1.0, methanol)
 ⑦ Ultraviolet absorption spectrum (as shown in FIG. 7)
  UV $\lambda_{max}^{methanol}$ nm (log ε): 266.5 (4.32), 368 (3.19).
  $\lambda_{min}^{methanol}$ nm (log ε): 230 (3.86), 330 (3.16).
 ⑧ Infrared absorption spectrum (as shown in FIG. 8)
  IR $\nu_{max}^{CHCl_3}$ cm$^{-1}$: 3400, 1720, 1685, 1655, 1615.
 ⑨ NMR spectrum (CDCl$_3$) (as shown in FIG. 9)
  δ: 1.86 (3H, S), 2.00 (3H, S), 2.38 (3H, S), 2.44 (3H, S), 3.46 (3H, S), 3.96 (3H, S), 6.60 (1H, bs).
 ⑩ Solubility
  Easily soluble: Lower alcohols, chloroform, esters, acetone, benzene
  Sparingly soluble: Ethyl ether
  Insoluble: Water, n-hexane
 ⑪ Color reaction
  Positive in Dragendorff and Meyer reactions, negative in ninhydrin and Ehrlich reactions

Figure 10:
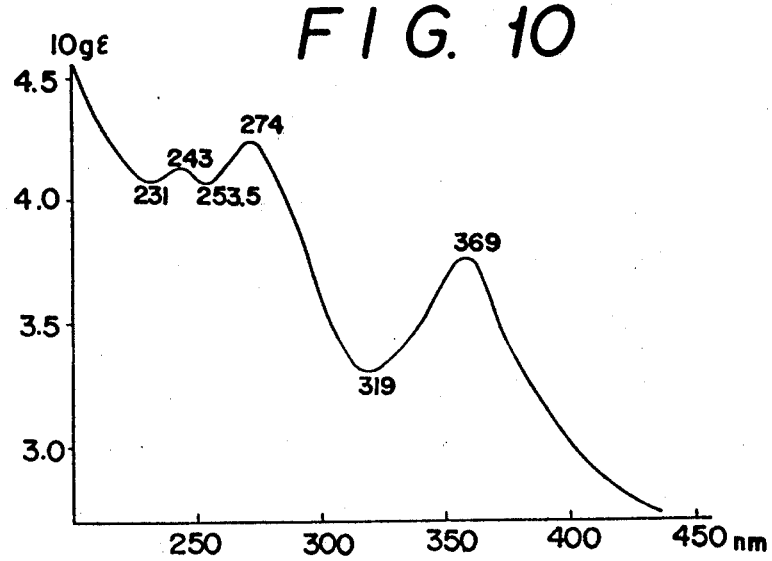
Figure 11:
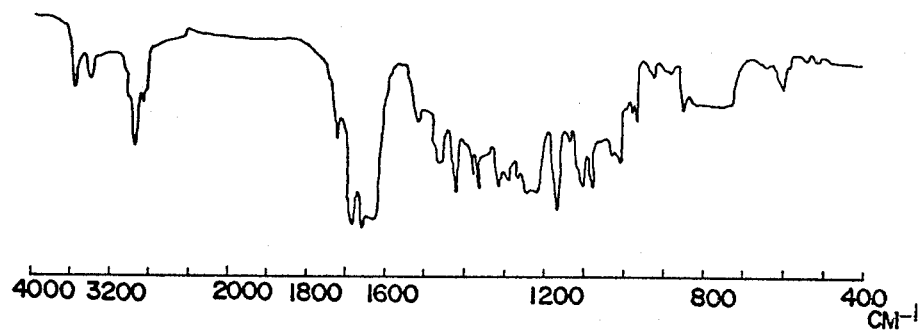
Figure 12:
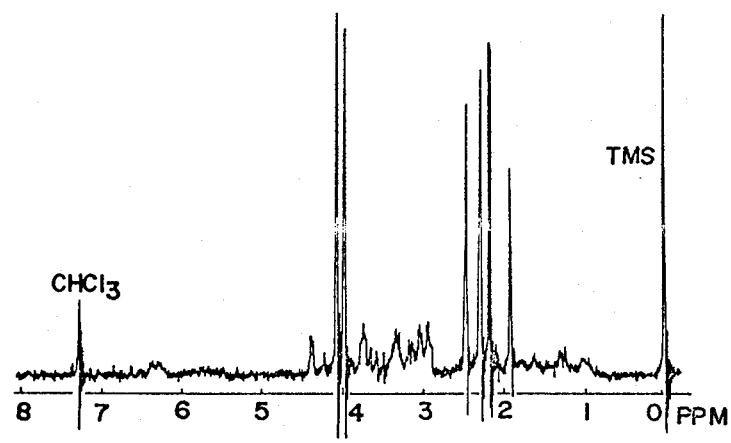

[D] Physico-chemical properties of saframycin D
 ① Color and appearance
  Yellow needles
 ② Melting point
  150°-154° C.
 ③ Elementary analysis
  C: 60.48%, H: 5.68%, N, 7.59%.
 ④ Molecular weight (Mass spectrum)
  553
 ⑤ Empirical formula
  $C_{28}H_{31}N_3O_9$
 ⑥ Specific rotation
  $[\alpha]_D^{20} = +141°$ (C=1.0, methanol)
 ⑦ Ultraviolet absorption spectrum (as seen in FIG. 10)
  UV $\lambda_{max}^{methanol}$ nm (log ε): 243 (4.14), 274 (4.24), 369 (3.75).
  $\lambda_{min}^{methanol}$ nm (log ε): 231 (4.08), 253 (4.06), 319 (3.30).
 ⑧ Infrared absorption spectrum (as seen in FIG. 11)
  IR $\nu_{max}^{CHCl_3}$ cm$^{-1}$: 3560, 3400, 1720, 1685, 1660, 1630.
 ⑨ NMR spectrum (CDCl$_3$) (as seen in FIG. 12)
  δ: 1.91 (3H, S), 2.17 (3H, S), 2.28 (3H, S), 2.45 (3H, S), 3.97 (3H, S), 4.06 (3H, S).
 ⑩ Solubility Easily soluble: Lower alcohols, chloroform, pyridine
Sparingly soluble: esters, acetone, ethyl ether
Insoluble: Water, n-hexane ⑪ Color reaction
Positive in Dragendorff reaction

[E] Physico-chemical properties of saframycin E

① Color and appearance
Yellow powder

② Melting point
146°–148° C.

③ Elementary analysis
C: 58.52%, H: 5.89%, N: 7.36%.

④ Molecular weight (converted upon mass spectrum of the corresponding triacetyl derivative) 555

⑤ Empirical formula
$C_{28}H_{33}N_3O_9 \cdot H_2O$

⑥ Specific rotation
$[\alpha]_D^{20} = -37.3°$ (C=0.53, methanol)

Figure 13:
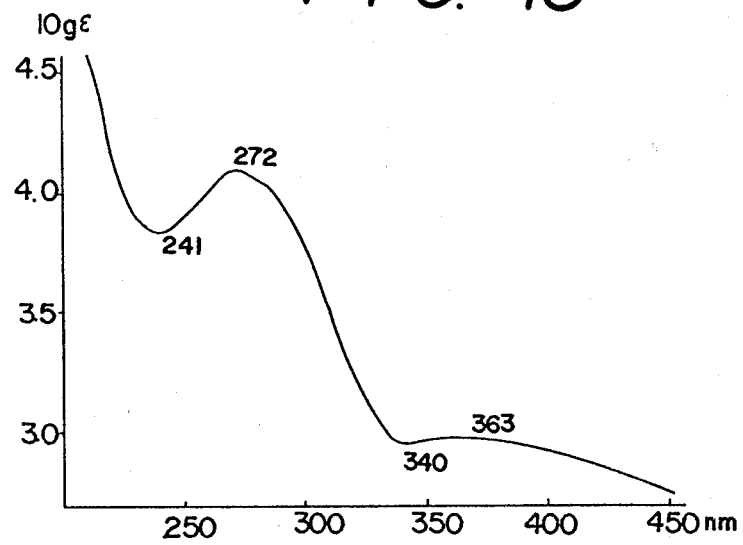

⑦ Ultraviolet absorption spectrum (as seen in FIG. 13)
UV $\lambda_{max}^{methanol}$ nm (log ε): 272 (4.10), 368 (2.93).
$\lambda_{min}^{methanol}$ nm (log ε): 241 (3.84), 340 (2.96).

Figure 14:
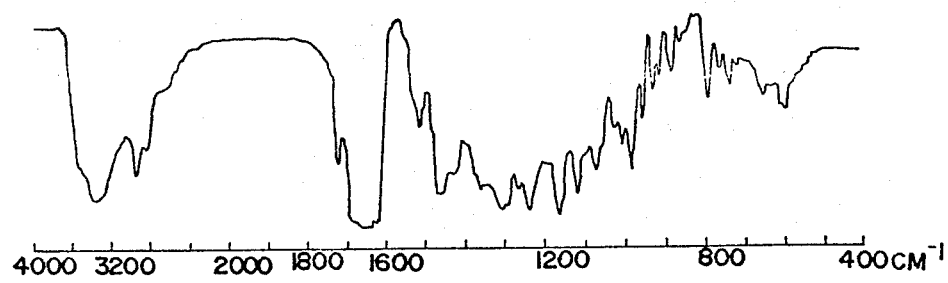

⑧ Infrared absorption spectrum (as seen in FIG. 14)
IR $\nu_{max}^{KBr}$ cm$^{-1}$: 3380, 1720, 1685, 1655, 1620.

Figure 15:
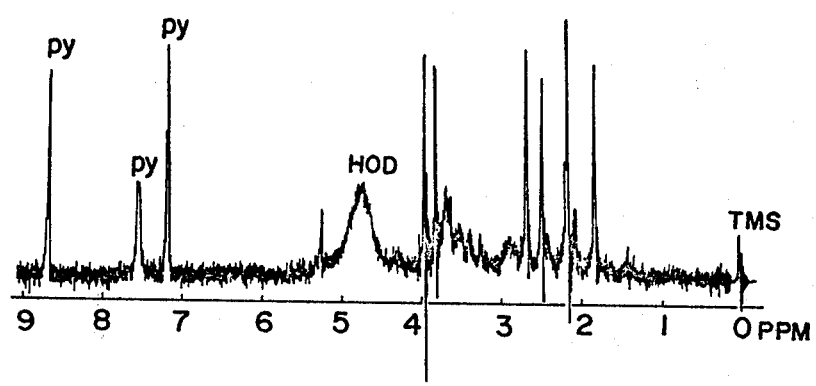

⑨ NMR spectrum (d-5 pyridine) (as seen in FIG. 15)
δ: 1.83 (3H, S), 2.17 (3H, S), 2.30 (3H, S), 2.48 (3H, S), 3.82 (3H, S), 3.95 (3H, S), 5.22 (1H, S).

⑩ Solubility
Easily soluble: Lower alcohols, pyridine
Sparingly soluble: Acetone, esters, chloroform
Insoluble: Water, n-hexane ⑪ Color reaction
Positive in Dragendorff reaction Saframycins A, B, C, D and E show as their biological activities antibacterial and activity against transplantable tumors and can be used as a medicament. Antibacterial spectra of saframycins A, B, C, D and E are given in Table 4. The antibiotics exhibit an antibacterial activity mainly against gram-positive bacteria, but only little if any activity against most gram-negative bacteria. Against the cultured cells of L 1210 in mouse leukemia, saframycin A can completely inhibit the cell growth at 0.02 μg/ml, saframycin B at 5 μg/ml and saframycins C, D and E at 20 μg/ml.

TABLE 4

Antimicrobial spectra of saframycins A, B, C, D and E

| Test organism | MIC (mcg/ml) | | | | |
|---|---|---|---|---|---|
| | A | B | C | D | E |
| Staphylococcus aureus 209P | 0.1 | 12.5 | 25.0 | 25.0 | 100.0 |
| Staphylococcus aureus Smith | 0.05 | 1.56 | 6.25 | 50.0 | 50.0 |
| Staphylococcus albus | 0.1 | 12.5 | 25.0 | 50.0 | 100.0 |
| Staphylococcus citreus | 0.1 | 12.5 | 25.0 | 50.0 | 100.0 |
| Streptococcus faecalis | 6.25 | >100.0 | >100.0 | — | >100.0 |
| Streptococcus pyogenes | 0.78 | 12.5 | 25.0 | — | >100.0 |
| Streptococcus pyogenes 090R | 6.25 | 25.0 | 12.5 | — | 25.0 |
| Staphylococcus salivarius | 6.25 | 100.0 | >100.0 | — | 100.0 |
| Micrococcus luteus | 0.05 | 1.56 | 6.25 | 50.0 | 12.5 |
| Bacillus subtilis | 0.1 | 25.0 | 25.0 | 50.0 | 100.0 |
| Bacillus cereus | 12.5 | 100.0 | 100.0 | 100.0 | 25.0 |
| Corynebacterium dephtheriae | <0.003 | 0.4 | 3.125 | 0.195 | 100.0 |
| Corynebacterium xerosis | <0.003 | 12.5 | 25.0 | 6.25 | 25.0 |
| Mycobacterium sp. 607 | 12.5 | 100.0 | >100.0 | 50.0 | 100.0 |
| Mycobacterium phlei | 25.0 | 50.0 | >100.0 | 50.0 | 25.0 |
| Mycobacterium avium | 12.5 | 100.0 | >100.0 | 50.0 | 100.0 |
| Nocardia asteroides | 6.25 | 50.0 | 50.0 | 50.0 | 25.0 |
| Escherichia coli | 50.0 | >100.0 | >100.0 | >100.0 | >100.0 |
| Salmonella typhimurium | 100.0 | >100.0 | >100.0 | >100.0 | >100.0 |
| Shigella dysenteriae Shiga | 25.0 | >100.0 | >100.0 | >100.0 | >100.0 |
| Klebsiella pneumoniae | 6.25 | 12.5 | 50.0 | 100.0 | 50.0 |
| Brucella abortus | 6.25 | 50.0 | 50.0 | 25.0 | 25.0 |
| Serratia marcescens | >100.0 | >100.0 | >100.0 | >100.0 | >100.0 |
| Pseudomonas aeruginosa | >100.0 | >100.0 | >100.0 | >100.0 | >100.0 |
| Mucor mucedo | >100.0 | >100.0 | >100.0 | >100.0 | >100.0 |
| Saccharomyces cerevisiae | >100.0 | >100.0 | >100.0 | >100.0 | >100.0 |
| Rhodotorula glutinis | >100.0 | >100.0 | >100.0 | >100.0 | >100.0 |
| Aspergillus niger | >100.0 | >100.0 | >100.0 | >100.0 | >100.0 |
| Aspergillus oryzae | >100.0 | >100.0 | >100.0 | >100.0 | >100.0 |
| Penicillium glaucum | 50.0 | >100.0 | >100.0 | >100.0 | >100.0 |
| Trichophyton mentagrophytes | >100.0 | >100.0 | >100.0 | >100.0 | >100.0 |
| Candida albicans | >100.0 | >100.0 | >100.0 | >100.0 | >100.0 |

Medium and Culture Condition:

1% glucose nutrient agar (3% glycerol nutrient agar for acid-fast bacteria, blood agar for *Streptococcus pyogenes* and *Brucella abortus*), 37° C., 24 or 48 hours.

Sabouraud.dextrose.agar for fungi, 27° C., 48 hours (72 hours for *Trichophyton mentagrophytes*).

Saframycins A, B, C, D and E are substances having a relatively low toxicity, which are tolerable in mice, average body weight of 18–20 g., via intravenous injection of Saframycin A to show LD$_{50}$=12 mg/kg and intraperitoneal injection to show LD$_{50}$=40 mg/kg, and via intraperitoneal injection of saframycin B, C, D or E at 250 mg/kg.

As saframycin A is most bioactive, its activity against transplantable tumors was further studied as shown below. When DDY mice were implanted with 1×10$^5$ cells of Ehrlich ascites tumor and daily intraperitoneal treatment of saframycin A at a dose of 0.5 mg/kg was initiated 24 hours after tumor implantation for 4 days, 30% of mice were cured and survived more than 30 days. With a dose of 1.0 mg/kg, 60% of mice was cured. The effects of saframycin A by intraperitoneal treatment on mouse lymphocytic leukemia L1210 and lymphoid leukemia P388 were studied with DBF$_1$ mice. When saframycin A treatment was started 3 hours after the intraperitoneal implantation of 1×10$^5$ cells of L1210 tumor, saframycin A at a daily dose of 1.5 mg/kg for 2 days produced T/C (survival period of treated group over survival period of control group) of 183%. With P388 tumor, the inoculum size of 1×10$^6$ cells was employed and the treatment was initiated after 24 hours. Saframycin A at a daily dose of 0.75 mg/kg for 10 days produced T/C of 219%. The effect of saframycin A was then studied against human tumors, two lines of uterine cervical carcinoma, melanoma, oat cell carcinoma and stomach carcinoma, heterotransplanted to nude mice.

Saframycin A was found to be selectively active on cervical carcinoma and stomach carcinoma producing the inhibition of tumor growth and significant histological changes in tumor tissue.

Assay

Antibacterial activities during cultivation and extraction procedures are assayed by an agar plate disc method using *Bacillus subtilis* PCI 219. Assay of streptothricin is conducted using *Escherichia coli* strain $F_1$, as the strain No. 314 can produce said antibiotic in a large amount. Co-existence of streptothricin can be easily detected by determination of an antibacterial activity against *E. coli*, as the saframycin complex, namely the fraction extracted into a solvent, has no activity against E. coli.

Some embodiments of the production of the present antibiotic substances will be shown by way of the following non-limiting examples.

EXAMPLE 1

Shaking culture in flasks

A. Seed Culture

A suspension of a freeze-dried preparation of *Streptomyces lavendulae* strain No. 314 in physiological saline was prepared and inoculated on agar slant having the following composition.

| | |
|---|---|
| Glucose | 10 g |
| L-asparagine | 5 g |
| $KH_2PO_4$ | 5 g |
| Agar | 15 g |
| Tap water | 1000 ml |
| pH | 6.8-7.0 |

Cultivation was continued at 27° C. for 1 week to afford a seed culture with abundant growth and many spores. B. Fermentation One hundred shaking flasks, each being of 500 ml-volume and containing 100 ml of the culture medium as defined below, were aseptically inoculated with the spores collected from the above seed culture in two loopfuls per flask.

| | |
|---|---|
| Glucose | 1.0 g |
| Starch | 10.0 g |
| Polypepton (available from Wako Pure Chemical Industries, Ltd., Japan) | 10.0 g |
| Meat extract (available) from Wako Pure Chemical Industries, Ltd., Japan) | 5.0 g |
| NaCl | 3.0 g |
| Silicon KM 72 (Shin-Etsu Chemical Co., Ltd., Japan) | 10 ml |
| Tap water | 1000 ml |
| pH | 7.0 |

Cultivation was effected at 27° C. for 40 hours by means of a reciprocal shaking apparatus (125 strokes per minute, 8 cm amplitude).

After completion of the cultivation, contents of the flasks were combined and mycelia were removed by means of a continuous centrifugal separator. The supernatant portion (10 l) thus obtained was adjusted to pH 8.0 and then extracted three times each with $\frac{1}{3}$ volume of chloroform.

The extracts were combined, filtered through a filter paper and then concentrated to dryness under reduced pressure to give 2.8 g. of a dark brown solid substance.

A solution of the substance in 50 ml. of ethyl acetate was shaken with 25 ml. of 1 N sodium carbonate to remove acidic substances. The organic layer was extracted five times with each 25 ml portion of 1 N hydrochloric acid. The ethyl acetate layer was concentrated to dryness to give 220 mg. of a neutral crude extract. The combined aqueous layers were adjusted to pH 8-9 with aqueous ammonia and extracted five times with each equal portion of chloroform. The organic layers were combined and again concentrated to dryness under reduced pressure to afford 91 mg. of a basic crude extract containing Saframycin complex.

The neutral crude extract (220 mg.) was subjected to column chromatography using 6 g. of silica gel (70-230 mesh, available from Merck & Co., W. Germany) and elution was effected with ethyl acetate:benzene (1:4) to give 110 mg. of fractions containing predominantly saframycin A. They were subjected to column chromatography using Sephadex LH-20 and methanol as an eluent to give 18 mg of saframycin A as a crude powder.

The basic crude extract (91 mg.) was column-chromatographed over 3 g. of silica gel (70-230 mesh, Merck & Co.), which was then developed successively with ethyl acetate:benzene (1:4), (1:1), ethyl acetate and ethyl acetate containing methanol at 5% to give in turn saframycins A, D, C, B and E, respectively. Each fraction was subjected to column chromatography using Sephadex LH-20 and methanol as an eluent to remove a major portion of contaminants. The saframycin A fraction and the above-mentioned saframycin A crude powder were combined and subjected repeatedly to column-chromatography using silica gel (230 mesh, Merck & Co.) to afford 11 mg. of a pure saframycin A powder. The respective fractions containing crude powders of saframycins B, C and D were subjected repeatedly to column chromatography using silica gel (230 mesh, Merck & Co.) to give 41 mg., 18 mg. and 6 mg. of saframycins B, C and D as crude powders, respectively. The crude powders were recrystallized from cold ether to give 21 mg., 8 mg. and 3 mg. of crystalline saframycins B, C and D, respectively. The fraction containing saframycin E was further subjected to column chromatography using Sephadex LH-20 and subsequently column chromatography using silica gel (230 mesh, Merck & Co.) repeatedly to afford 18 mg. of saframycin E as a crude powder, which was then recrystallized from acetone to yield 3 mg. of pure saframycin E as a powder.

EXAMPLE 2

Fermentation in jar fermentors

A. A seed culture was prepared in the same manner as in Example 1 except that cultivation was effected for 24 hours.

B. Four jar fermentors, each being of 20 l. - volume and containing 15 l. of the culture medium as defined below, were sterilized under pressure in a conventional manner.

| | |
|---|---|
| Glucose | 5.0 g |
| Starch | 5.0 g |
| Polypepton (available from Wako Pure Chemical Industries, Ltd., Japan) | 10.0 g |
| Meat extract (available from Wako Pure Chemical | 5.0 g |

| Industries, Ltd., Japan) | |
|---|---|
| NaCl | 3.0 g |
| Tap water | 1000 ml |
| pH | 7.0-7.2 |

Cultivation was continued for 18 hours under the following condition.

| Seed culture | 1% |
|---|---|
| Cultivation temperature | 27° C. |
| Agitation | 550 rpm |
| Flow rate of aseptic air | 1 volume of medium per min. |
| Antifoaming agent (Silicon KM 72) | Added, if necessary |

After the lapse of the above time, the maximum potency of the produced saframycin complex was obtained and thereafter the titer rapidly decreased. The pH of the cultured broth dropped below 6.0 and thereafter rose to approximately 6.8. Mycelium volume rapidly increased and the glucose was almost exhausted at that time. At the maximum potency of saframycin, a dilution method using Bacillus subtilis PCI 219 as test organism showed 512 dilution unit and an agar plate diffusion method showed an inhibition zone of about 40 mm. The maximum production of streptothricin was achieved later, in about 30 hours. From the cultured broth (about 240 l.) pooled from the jar fermentors were removed mycelia by means of a continuous centrifugal separator and the culture liquid was concentrated to ⅛ volume by means of Contro concentration apparatus (an instantaneous concentration apparatus under reduced pressure).

The filtrate was adjusted to pH 8.0 with a 1 N aqueous solution of sodium hydroxide. Then, the adjusted filtrate was extracted three times with an equal volume of methylene dichloride with stirring at intervals of 1 hour. The organic layers were separated, combined and concentrated under reduced pressure to dryness to give 16.4 g. of crude saframycin complex. The complex was subjected three times to a counter-current distribution method using methanol-n-hexane. The methanol layers were combined and concentrated under reduced pressure to dryness. The residue was dissolved in 200 ml. of benzene and well washed twice by shaking with 100 ml. of 1 N sodium carbonate. The washed benzene layer was shaken five times with each 60 ml. portion of 1 N hydrochloric acid to transfer a basic substance thereinto. The hydrochloric acid layers were combined, adjusted to pH 8-9 again with aqueous ammonia and then extracted five times with an equal volume of chloroform. The organic layer was separated and concentrated to dryness under reduced pressure to give 2.7 g. of crude basic extract. The benzene layer was concentrated to dryness to leave 2.7 g. of neutral crude extract. A total amount of the crude product thus prepared from 4 jar fermentors varied from about 0.2 g. to 1.2 g.

Cultivation was repeated 20 times using 4 jar fermentors and a total amount of the cultured broth of 1200 l, thereby yielding 12.4 g. of the crude neutral extract and 12.6 g. of the crude basic extract.

Isolation and purification of saframycins A, B, C, D and E from the so obtained extracts were effected, for instance, as mentioned below.

The neutral crude extract (12.4 g.) was subjected to column chromatography using 120 g. of silica gel (70-230 mesh, Merck & Co.) and ethyl acetate:benzene (1:4) as an eluent to produce 1.2 g. of the fraction containing saframycin A, which was then subjected to column chromatography using Sephadex LH-20 and methanol as an eluent to afford 220 mg. of crude powdery saframycin A.

The basic crude extract (12.8 g.) was subjected to column chromatography using silica gel (70-230 mesh, Merck & Co.) and ethyl acetate:benzene (1:1) as an eluent, thereby a major portion of contaminants being adsorbed on the column. The eluate containing saframycin complex was further subjected to column chromatography using Sephadex LH-20 to remove a major portion of contaminants, thereby leaving 6.3 g. of the fraction containing 6.3 g. of saframycin complex. The fraction was column-chromatographed over 180 g. of silica gel (70-230 mesh, Merck & Co.) with successive development of ethyl acetate:benzene (1:4); ethyl acetate:benzene (1:1); ethyl acetate; and ethyl acetate containing 5% methanol to give in turn saframycins A, B, C, D and E, respectively. Each fraction was column-chromatographed over Sephadex LH-20 with methanol as an eluent to remove a major portion of contominants, thereby yielding 52 mg. of the fraction of saframycin A. This fraction and 220 mg. of the above-mentioned saframycin A crude powder were combined and repeatedly column-chromatographed over silica gel (230 mesh, Merck & Co.) to produce 142 mg. of the crude powder of saframycin A, which was then recrystallized from a cold ether to give 72 mg. of pure saframycin A.

The respective fractions containing saframycins B, C, D and E were separately chromatographed repeatedly by the use of silica gel (230 mesh, Merck & Co.) column and Sephadex LH-20 column to give 590 mg. of saframycin B, 60 mg. of saframycin C, 29 mg. of saframycin D and 29 mg. of saframycin E as the crude powders, respectively. They were respectively recrystallized from a cold ether to produce 411 mg. of saframycin B, 32 mg. of saframycin C and 12 mg. of saframycin D, while recrystallization of the crude saframycin E from acetone gave 9 mg. of saframycin E as a pure powder.

What is claimed is:

1. An antibiotic substance, saframycin A, having the following physico-chemical characteristics:
   Color and appearance:
   Yellow powder in saframycin A base form;
   Melting point:
   122°-126° C.;
   Elementary analysis:
   C: 61.47%, H: 5.41%, N: 9.33%;
   Molecular weight according to mass spectrum:
   562;
   Empirical formula:
   $C_{29}H_{30}N_4O_8 \cdot 2/5\ H_2O$;
   Specific rotation:
   $[\alpha]_D^{20} = +18.2°$ (C=1.0, methanol);
   Ultraviolet absorption spectrum as shown in FIG. 1:
   UV $\lambda_{max}^{methanol}$ nm (log $\epsilon$): 267 (4.34) $\lambda_{min}^{methanol}$ nm (log $\epsilon$): 230 (3.88);
   Infrared absorption spectrum as shown in FIG. 2:
   IR $\lambda_{max}^{CHCl_3}$ cm$^{-1}$: 3400, 1716, 1685, 1660, 1615;
   NMR spectrum (CDCl$_3$) as shown in FIG. 3:
   $\delta$: 1.90 (3H, S), 1.98 (3H, S), 2.24 (3H, S), 2.30 (3H, S), 4.04 (6H, S), 6.65 (3H, bs);
   Solubility:
   Easily soluble: Esters, chloroform, acetone, alcohols
   Sparingly soluble: Ethyl ether Insoluble: Water, n-hexane; and
Color reaction:
Positive in Dragendorff reaction; negative in ninhydrin, perchloroiron and anthrone reactions.

2. An antibiotic substance, saframycin B, having the following physico-chemical characteristics:
Color and appearance:
   orange-yellow prisms;
Melting point:
   108°–109° C.;
Elementary analysis:
   C: 62.36%, H: 5.71%, N: 7.66%;
Molecular weight according to mass spectrum:
   537;
Empirical formula:
   $C_{28}H_{31}N_3O_8$;
Specific rotation:
   $[\alpha]_D^{20} = -54.4$ (C=1.0, methanol);
Ultraviolet absorption spectrum as shown in FIG. 4:
   UV $\lambda_{max}^{methanol}$ nm (log $\epsilon$): 269 (4.35), 368 (3.13).
   $\lambda_{min}^{methanol}$ nm (log $\epsilon$): 232 (3.86), 330 (3.10);
Infrared absorption spectrum as shown in FIG. 5:
   IR $\nu_{max}^{CHCl_3}$ cm$^{-1}$: 3430, 1720, 1690, 1660, 1620;
NMR spectrum (CDCl$_3$) as shown in FIG. 6:
   $\delta$: 1.90 (3H, S), 1.98 (3H, S), 2.23 (3H, S), 2.28 (3H, S), 4.00 (6H, S), 6.28 (1H, bs);
Solubility:
Easily soluble: Lower alcohols, chloroform, esters, acetone, benzene
Sparingly soluble: Ethyl ether
Insoluble: Water, n-hexane; and
Color reaction:
   Positive in Dragendorff and Meyer reactions, negative in ninhydrin and Ehrlich reactions.

3. An antibiotic substance, saframycin C, having the following physico-chemical characteristics:
Color and appearance:
   Orange-red needles;
Melting point:
   143°–146° C.;
Elementary analysis:
   C: 61.61%, H: 5.96%, N: 7.39%;
Molecular weight according to mass spectrum:
   567;
Empirical formula:
   $C_{29}H_{33}N_3O_9$;
Specific rotation:
   $[\alpha]_D^{20} = -20.8°$ (C=1.0, methanol);
Ultraviolet absorption spectrum as shown in FIG. 7:
   UV $\lambda_{max}^{methanol}$ nm (log $\epsilon$): 266.5 (4.32), 368 (3.19).
   $\lambda_{min}^{methanol}$ nm (log $\epsilon$): 230 (3.86), 330 (3.16);
Infrared absorption spectrum as shown in FIG. 8:
   IR $\nu_{max}^{CHCl_3}$ cm$^{-1}$: 3400, 1720, 1685, 1655, 1615;
NMR spectrum (CDCl$_3$) as shown in FIG. 9:
   $\delta$: 1.86 (3H, S), 2.00 (3H, S), 2.38 (3H, S), 2.44 (3H, S), 3.46 (3H, S), 3.96 (3H, S), 6.60 (1H, bs);
Solubility:
Easily soluble: Lower alcohols, chloroform, esters, acetone, benzene
Sparingly soluble: Ethyl ether
Insoluble: Water, n-hexane; and
Color reaction:
   Positive in Dragendorff and Meyer reactions, negative in ninhydrin and Ehrlich reactions.

4. An antibiotic substance, saframycin D, having the following physico-chemical characteristics:
Color and appearance:
   Yellow needles;
Melting point:
   150°–154° C.;
Elementary analysis:
   C: 60.48%, H: 5.68%, N: 7.59%;
Molecular weight according to mass spectrum:
   553;
Empirical formula:
   $C_{28}H_{31}N_3O_9$;
Specific rotation:
   $[\alpha]_D^{20} = +141°$ (C=1.0, methanol);
Ultraviolet absorption spectrum as seen in FIG. 10:
   UV $\lambda_{max}^{methanol}$ nm (log $\epsilon$): 243 (4.14), 274 (4.24), 369 (3.75).
   $\lambda_{min}^{methanol}$ nm (log $\epsilon$): 231 (4.08), 253 (4.06), 319 (3.30);
Infrared absorption spectrum as seen in FIG. 11:
   IR $\nu_{max}^{CHCl_3}$ cm$^{-1}$: 3560, 3400, 1720, 1685, 1660, 1630;
NMR spectrum (CDCl$_3$) as seen in FIG. 12:
   $\delta$: 1.91 (3H, S), 2.17 (3H, S), 2.28 (3H, S), 2.45 (3H, S), 3.97 (3H, S), 4.06 (3H, S);
Solubility:
Easily soluble: Lower alcohols, chloroform, pyridine
Sparingly soluble: esters, acetone, ethyl ether
Insoluble: Water, n-hexane; and
Color reaction:
   Positive in Dragendorff reaction.

5. An antibiotic substance, saframycin E, having the following physico-chemical characteristics:
Color and appearance:
   Yellow powder;
Melting point:
   146°–148° C.;
Elementary analysis:
   C: 58.52%, H: 5.89%, N: 7.36%;
Molecular weight (converted upon mass spectrum of the corresponding triacetyl derivative):
   555;
Empirical formula:
   $C_{28}H_{33}N_3O_9 \cdot H_2O$;
Specific rotation:
   $[\alpha]_D^{20} = -37.3°$ (C=0.53; methanol);
Ultraviolet absorption spectrum as seen in FIG. 13:
   UV $\lambda_{max}^{methanol}$ nm (log $\epsilon$): 272 (4.10), 368 (2.93).
   $\lambda_{min}^{methanol}$ nm (log $\epsilon$): 241 (3.84), 340 (2.96);
Infrared absorption spectrum as seen in FIG. 14:
   IR $\nu_{max}^{KBr}$ cm$^{-1}$: 3380, 1720, 1685, 1655, 1620;
NMR spectrum (d-5 pyridine) as seen in FIG. 15:
   $\delta$: 1.83 (3H, S), 2.17 (3H, S), 2.30 (3H, S), 2.48 (3H, S), 3.82 (3H, S), 3.95 (3H, S), 5.22 (1H, S);
Solubility:
Easily soluble: Lower alcohols, pyridine
Sparingly soluble: Acetone, esters, chloroform
Insoluble: Water, n-hexane; and
Color reaction:
   Positive in Dragendorff reaction.

6. A pharmaceutical composition which comprises an antibacterially effective amount of saframycin A as defined in claim 1 or acid addition salts thereof, together with a pharmaceutical carrier or excipient.

7. A pharmaceutical composition which comprises an antibacterially effective amount of saframycin B as defined in claim 2 or acid addition salts thereof, together with a pharmaceutical carrier or excipient.

8. A pharmaceutical composition which comprises an antibacterially effective amount of saframycin C as defined in claim 3 or acid addition salts thereof, together with a pharmaceutical carrier or excipient.

9. A pharmaceutical composition which comprises an antibacterially effective amount of saframycin D as defined in claim 4 or acid addition salts thereof, together with a pharmaceutical carrier or excipient.

10. A pharmaceutical composition which comprises an antibacterially effective amount of saframycin E as defined in claim 5 or acid addition salts thereof, together with a pharmaceutical carrier or excipient.

* * * * *

UNITED STATES PATENT AND TRADEMARK OFFICE
CERTIFICATE OF CORRECTION

PATENT NO. : 4,248,863       Page 1 of 2
DATED : February 3, 1981
INVENTOR(S) : TADASHI ARAI It is certified that error appears in the above—identified patent and that said Letters Patent is hereby corrected as shown below:

Column 5, TABLE 2, line 14, in each of the three right-hand columns, insert --  -  --.

Column 5, TABLE 3, lines 28-42, replace all of the subject matter of the TABLE on these lines with the following TABLE.

| | | | |
|---|---|---|---|
| D-xylose* | − | ± | − |
| L-arabinose* | + | − | − |
| L-rhamnose* | − | − | − |
| D-glucose* | + | + | + |
| D-fructose* | ± | ± | − |
| sucrose* | + | + | + |
| lactose | − | − | − |
| maltose | + | + | + |
| raffinose* | − | − | − |
| mannitol* | − | − | − |

UNITED STATES PATENT AND TRADEMARK OFFICE
CERTIFICATE OF CORRECTION

PATENT NO. : 4,248,863
DATED : February 3, 1981
INVENTOR(S) : TADASHI ARAI

It is certified that error appears in the above—identified patent and that said Letters Patent is hereby corrected as shown below:

| | | | |
|---|---|---|---|
| i-inositol* | – | – | – |
| sodium acetate | + | + | + |
| sodium citrate | + | + | + |
| sodium succinate | + | + | + |
| Control | – | – | – |

* carbon source described in ISP.

Signed and Sealed this

Fifteenth Day of June 1982

[SEAL]

Attest:

GERALD J. MOSSINGHOFF

Attesting Officer — Commissioner of Patents and Trademarks